US00PP26249P2

(12) United States Plant Patent
Bakale, Jr.

(10) Patent No.: US PP26,249 P2
(45) Date of Patent: Dec. 22, 2015

(54) *HYDRANGEA* PLANT NAMED 'LINDSEY ANN'

(50) Latin Name: *Hydrangea macrophylla*
Varietal Denomination: Lindsey Ann

(71) Applicant: John David Bakale, Jr., Allendale, MI (US)

(72) Inventor: John David Bakale, Jr., Allendale, MI (US)

(73) Assignee: ATJ HOLDINGS, LLC, West Olive, MI (US)

( * ) Notice: Subject to any disclaimer, the term of this patent is extended or adjusted under 35 U.S.C. 154(b) by 0 days.

(21) Appl. No.: 13/986,417

(22) Filed: Apr. 30, 2013

(51) Int. Cl.
*A01H 5/02* (2006.01)

(52) U.S. Cl.
USPC ..... Plt./250

(58) Field of Classification Search
USPC ..... Plt./250
CPC ..... A01H 5/02
See application file for complete search history.

(56) References Cited

U.S. PATENT DOCUMENTS

| | | | |
|---|---|---|---|
| PP20,019 | P2 | 5/2009 | Wood |
| PP21,668 | P3 | 1/2011 | Higaki |
| PP21,942 | P3 | 5/2011 | Rampp |
| PP25,106 | P2 | 11/2014 | Hill |
| PP25,209 | P2 | 1/2015 | Ulrich |

OTHER PUBLICATIONS

'Dreamin' of the 'perfect' *Hydrangea*, 2012.*
Webpage entitled "L.A. Dreamin'™ *Hydrangea macrophylla* 'Lindsey Ann'," posted on www.gardencrossings.com date Jun. 21, 2012 from Internet archive website https;//web,archive.org/web/20120621105645/http://www.gardencrossings.com/plantname/Hydrangea-LA-Dreamin-Lindsey-Ann, dated Feb. 10, 2015.
Internet Archive webpage showing the different occasions the webpage entitled "L.A. Dreamin'™ *Hydrangea macrophylla* 'Lindsey Ann'," posted on www.gardencrossings.com was captured by the Internet Archive website, including the version captured on Jun. 21,2012 https://web.archive.org/web/20120621105645/http://www.gardencrossings.com/plantname/Hydrangea-LA-Dreamin-Lindsey-Ann, date Feb. 10, 2015.

* cited by examiner

*Primary Examiner* — Keith O. Robinson
(74) *Attorney, Agent, or Firm* — J. Bennett Mullinax, LLC

(57) ABSTRACT

A new and distinct cultivar of *Hydrangea* plant known by the varietal name 'Lindsey Ann', characterized by multiple unique flowers which will then produce new flowered sepals having, pink, mauve and blue colors.

8 Drawing Sheets

Botanical classification: *Hydrangea macrophylla.*
Varietal denomination: 'LINDSEY ANN'.

BACKGROUND OF THE INVENTION

The present invention relates to a new and distinct cultivar of *Hydrangea* plant botanically known as *Hydrangea macrophylla* and hereinafter referred to by the cultivar name 'Lindsey Ann'. The new variety was discovered in the spring of 1998 in a cultivated location in Allendale, Mich. It was observed to be a unique multicolored *Hydrangea* with good cold temperature hardiness. Softwood cuttings were first taken in June 2002 and rooted in West Olive, Mich. Asexual reproduction of the new cultivar by softwood cuttings since June 2002 in West Olive, Mich. has demonstrated that the new cultivar reproduces true to type with all of the characteristics, as herein described, firmly fixed and retained through successive generations of such asexual reproduction.

The following traits distinguish 'Lindsey Ann' as a new and distinct cultivar from other *Hydrangea* varieties known to the breeder:

1. Produces two unique floral sepals with one type of flower having deeply serrated sepals while adjacent flowers will have smooth sepal on an adjacent flower;
2. Produces multiple unique flowers which will then produce new flowered sepals having pink, mauve, and blue colors.

For example, Plants of the new *Hydrangea* can be compared to plants of the *Hydrangea macrophylla* 'Nikko Blue', not patented. Plants of the new *Hydrangea* differed from plants of 'Nikko Blue' in the following characteristics:

1. Plants of the new *Hydrangea* have an inflorescence color different from plants of 'Nikko Blue':
2. Plants of the new *Hydrangea* have darker green-colored, glossier leaves than plants of 'Nikko Blue'; and
3. Plants of the new *Hydrangea* had larger inflorescences than plants of 'Nikko Blue'.

Similarly, Plants of the new *Hydrangea* can be compared to plants of the *Hydrangea macrophylla* 'Penny Mac', not patented. Plants of the new *Hydrangea* differed from plants of 'Penny Mac' in the following characteristics:

1. Plants of the new *Hydrangea* have an inflorescence color different from plants of 'Penny Mac':
2. Plants of the new *Hydrangea* have darker green-colored, glossier leaves than plants of 'Penny Mac'; and
3. Plants of the new *Hydrangea* had larger inflorescences than plants of 'Penny Mac'.

DESCRIPTION OF THE DRAWING

The accompanying photographic drawings illustrate the new variety, with the color being as nearly true as is possible with color illustrations of this type.

DETAILED BOTANICAL DESCRIPTION

The following detailed description sets forth characteristics of the new cultivar. The plants were grown in 15 cm. pots, in standard potting soil with granulated fertilizers at a pH of 6.0. The plants were 6 Years old when described. Measuring and color reading of the plants were taken in Michigan, USA under natural light.

Plant:

*Time to initiate roots.*—About 10-14 days at 22° C.

*Rooting habit.*—Fibrous, dense and freely branching.

*Time to produce a young plant from a roots cutting.*—About 40-50 days.

*Form.*—Perennial shrub with very broad shape and strong lateral branching.

*Height* (*from media surface to top of foliage*).—60-77 cm.

*Height* (*from media surface to top of the flowers*).—76-81 cm.

*Plant diameter.*—60-77 cm.

*Vigor.*—Good.

*Strength.*—Good.

*Branching habit.*—Strong lateral branching.

Trunk:

*Main trunk length.*—60-70 cm.

*Diameter.*—6 mm.

Figure 1:
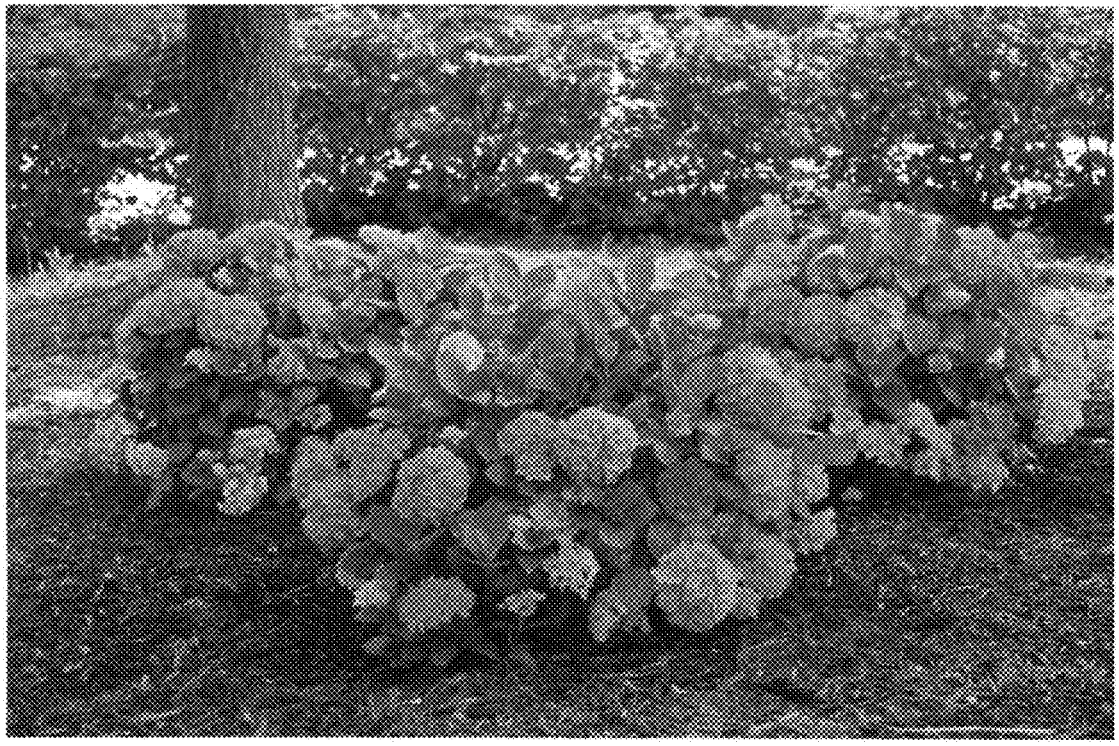
FIG. 1 is a photograph of the new variety
Figure 2:
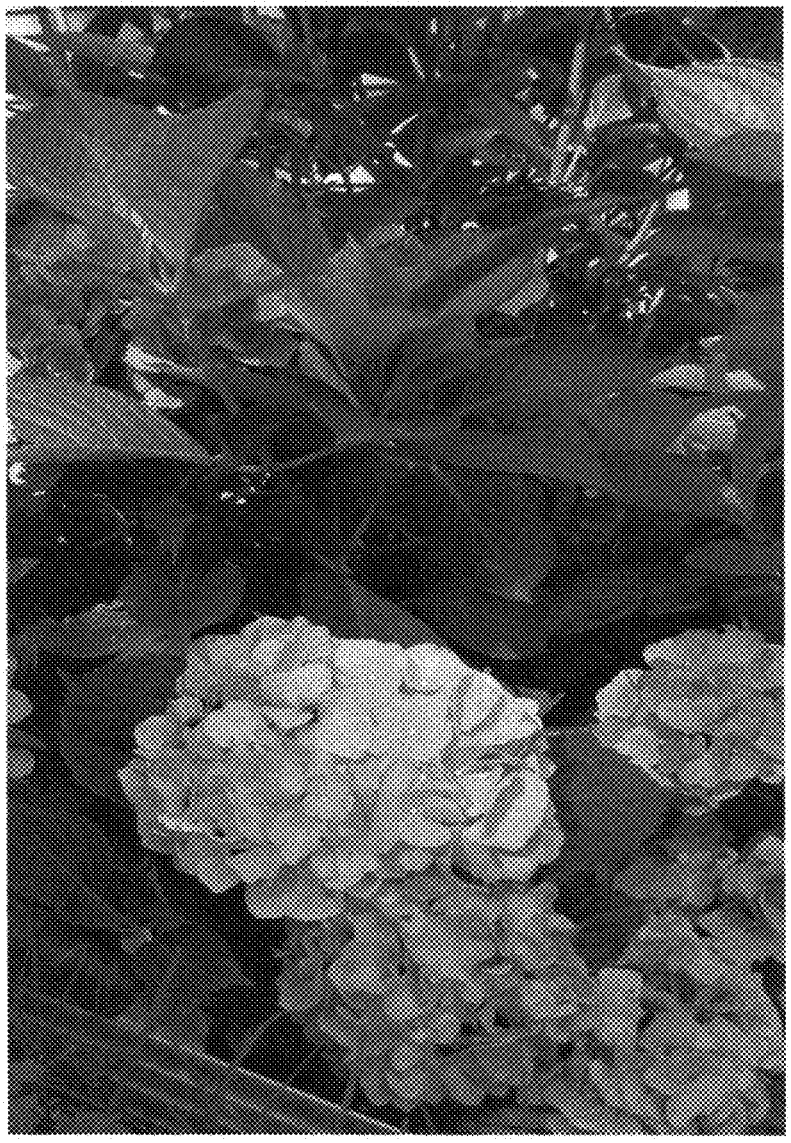
FIG. 2 is a close-up photograph of an inflorescence of the new variety
Figure 3:
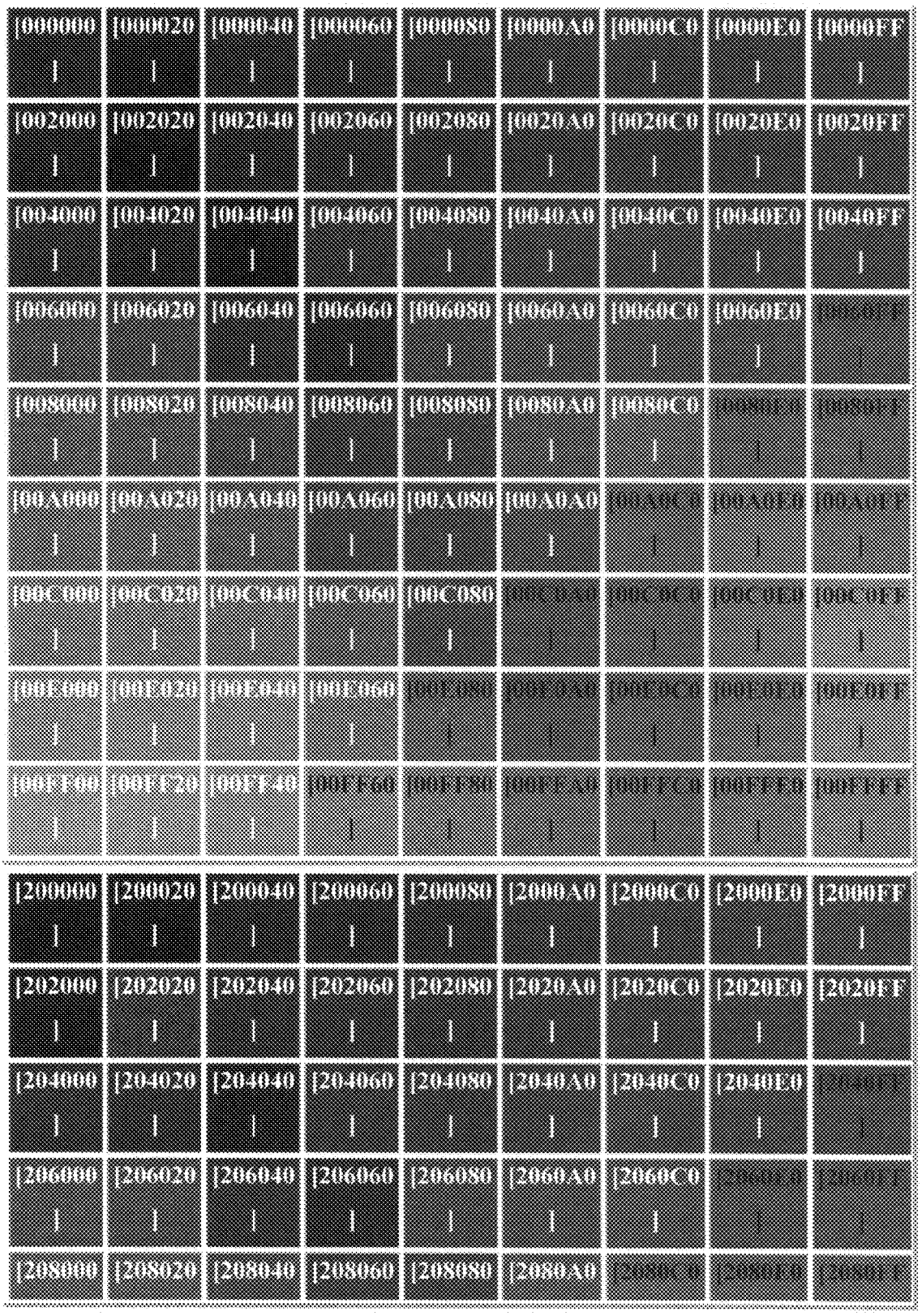
FIG. 3 is an HTML Color Chart (a color reference) which stands for HyperText Markup Language Color Chart and which was published Apr. 3, 2013; the said HTML Color Chart incorporated herein by reference.

*Color.*—A08060 (Refer to FIG. 3 for all colors).

*Texture.*—Smooth.

*Pubescence.*—Absent.

*Internode length.*—2.5 cm.

Lateral branches:

*Length.*—Young: 5 cm. Mature: 30 cm.

*Diameter.*—Young: 5 mm. Mature: 9 mm.

*Internode length.*—3-9 cm.

*Texture.*—Shiny.

*Pubescence.*—Absent.

*Color.*—Young: C0C080. Mature: 604020 (FIG. 3).

Foliage:

*Arrangement.*—Opposite single.

*Stipules.*—NA.

*Size of the leaf.*—Length 18 cm. Width: 11.5 cm.

*Shape of leaf* (*generally*).—Young Elliptic. Mature Elliptic.

*Shape of apex.*—Short acuminate.

*Shape of base.*—Cuneate.

*Texture.*—Shiny with satin finish on the upper surface of the leaf; the lower surface dull.

*Margin type.*—Serrate with base entire.

*Pubescence.*—None present — Glabrous.

*Color.*—Young leaves: Upper surface 04000. Lower Surface: 406020. (FIG. 3). Mature leaves: Upper Surface 04000. Lower surface 406000. (FIG. 3).

*Petiole.*—Shape: D Shaped. Length: 2-3 cm. Diameter: 5 mm. Color: A0C040 (FIG. 3).

*Veins* (*venation-pinnate*).—Color; Upper surface: C0C060. Lower Surface:C0C060 (FIG. 3).

Flower:

*Natural flowering season.*—June through early to mid-November in Michigan, USA.

*Blooming habit.*—Continuous.

*Bud.*—Shape of Cluster: Round. Diameter of cluster: 3.5-5 cm. Number of buds per cluster: 95. Shape: Flat Globe. Length: 2 mm. Width: 2 mm.

Inflorescence:

*Shape.*—Round panicle, Mophead type panicle.

*Depth.*—12 cm.

*Diameter.*—18-21 cm.

*Average number of flowers per inflorescence.*—Approximately 95.

*Average number of inflorescence per plant.*—45-50, depending on frost conditions that year.

*Lastingness of an individual flower.*—3 months.

*Lastingness of an inflorescences.*—3 months.

Petals: See petaloid sepals.

Petaloid sepals:

*Number per flower.*—4.

*Color.*—Upper Surface: Multi colored shades of Blue, Pink, and Mauve. Shades of Blue: 4020FF, 4040FF, 4060FF, 4080FF, 40A0FF, 40A0E0, 4080E0, 2040FF, 2040E0, 2040C0, 2020E0, 2000E0, 0060C0, 0060E0, 0060FF, 0080E0, 0080FF, 80E0FF, 80FFFF, A0FFFF, 80C0FF (FIG. 3). Shades of Mauve: E000FF, E020FF, E040FF, C000E0, 600060, 6040C0, 6020E0, 6000A0, 600080, 602080 (FIG. 3). Shades of Pink: FFC0FF, E0A0C0, E0A0E0 (FIG. 3). Lower surface: Multi colored shades of Blue, Pink, and Mauve. Shades of Blue: 40A0C0, 60C0E0, 60E0E0, 60C0FF, 60E0FF, 60FFFF, 80C0E0, 80C0FF, 80E0FF, 80FFFF (FIG. 3). Shades of Mauve: 6080C0, 6080E0, A080C0, A060E0, A060FF, A080E0, A080FF, A0A0C0, A0A0E0, A0A0FF, E080E0, E0A0E0, E0A0FF, E0C0E0, E0C0FF (FIG. 3). Shades of Pink: E0C0E0, FFA0E0, FFA0FF, FFC0E0, FFC0FF, FFE0FF, FFE0E0 (FIG. 3).

*Shape.*—Obtuse.

*Length.*—2-3 cm.

*Width.*—1.5-3 cm.

*Apex.*—(Shape) Acute.

*Base.*—(Shape) Obtuse.

*Margin.*—Irregular serrate.

*Texture.*—Smooth.

*Fused.*—No.

Petaloids: NA.

Peduncles:

*Length.*—2-3 cm.

*Diameter.*—3 mm.

*Texture.*—Sparsely pubescent.

*Color.*—E0FFC0 (FIG. 3).

Pedicels, sterile and fertile flowers:

*Length.*—About 2.8 cm.

*Diameter.*—About 1.8 mm.

*Strength.*—Strong.

*Texture.*—Glabrous.

*Color.*—E0FFC0 (FIG. 3).

Stamens:

*Number per fertile flower.*—8.

*Filament length.*—0.5-1.0 mm.

*Anthers shape.*—Oblong. Length 1 mm.

*Color.*—FFFFE0 (FIG. 3).

*Pollen color.*—FFFFE0 (FIG. 3).

Pistils:

*Number.*—1.

*Length.*—25 mm.

*Style.*—Less than 1 mm.

*Stigma number.*—2-parted. Shape: Compact. Color: FFFFE0 (FIG. 3). Size: less than 1 mm.

*Ovaries* (*half inferior*).—Length: 2 mm. Width: 1 mm. Color: FFFFE0 (FIG. 3).

*Fragrance.*—None.

Disease resistance: Resistance to the leaf spot, *Bipolaris sorokiniana*, and the blight, *Erysiphe graminis*.

Temperature tolerance: Very good; resistance to scorch in full sun; plant of the new *Hydrangea* have been shown to tolerate temperatures between −26° C. and 40° C.

Drought tolerance: Average.

It is claimed:

1. A new and distinct variety of *Hydrangea* plant substantially as illustrated and described herein.

* * * * *

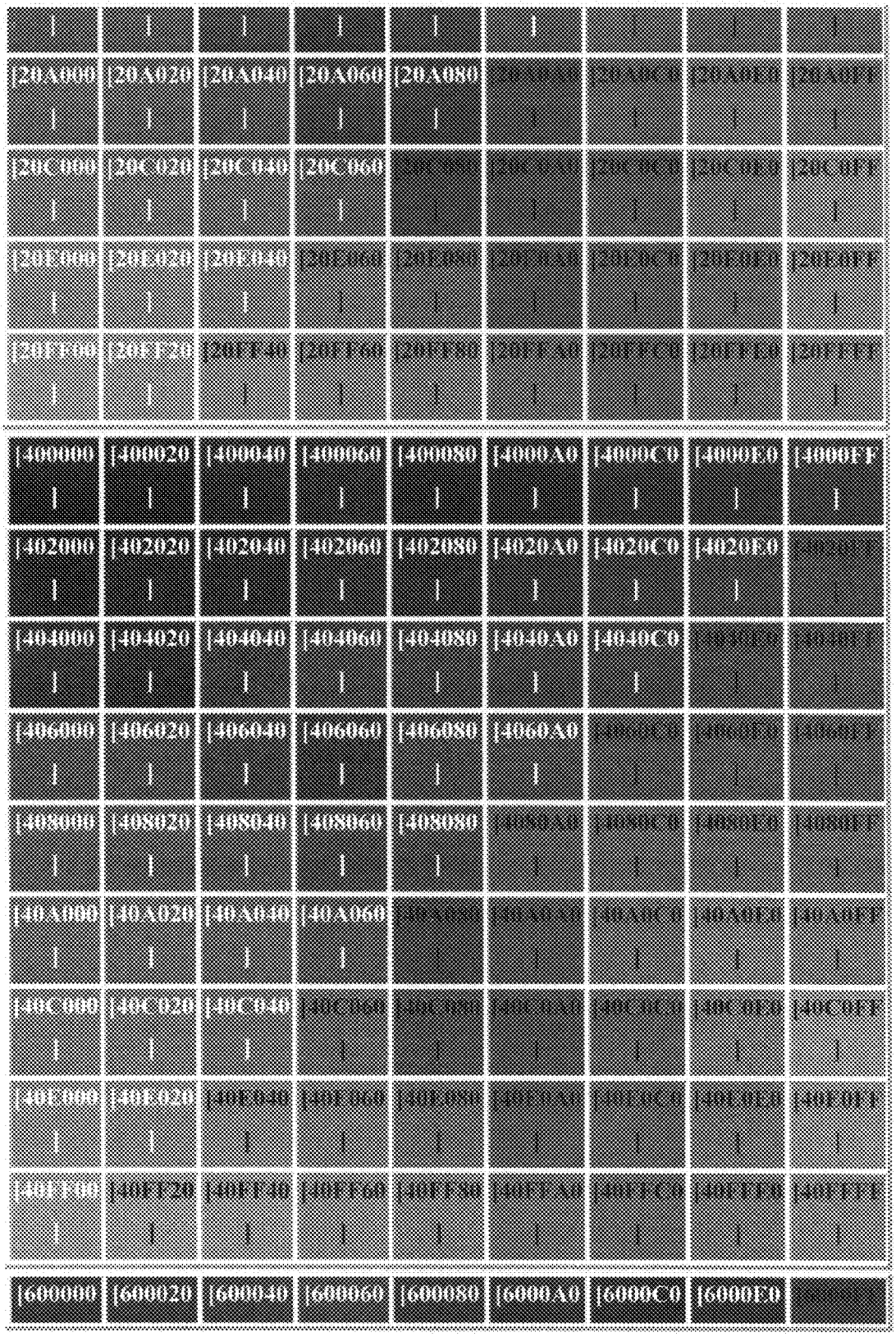
[20A000]
[20A020]
[20A040]
[20A060]
[20A080]
[20A0A0]
[20A0C0]
[20A0E0]
[20A0FE]
[20C000]
[20C020]
[20C040]
[20C060]
[20C080]
[20C0A0]
[20C0C0]
[20C0E0]
[20C0FE]
[20E000]
[20E020]
[20E040]
[20E060]
[20E080]
[20E0A0]
[20E0C0]
[20E0E0]
[20E0FE]
[20EF00]
[20EF20]
[20EF40]
[20EF60]
[20EF80]
[20EFA0]
[20EFC0]
[20EFE0]
[20EFFE]
[400000]
[400020]
[400040]
[400060]
[400080]
[4000A0]
[4000C0]
[4000E0]
[4000FE]
[402000]
[402020]
[402040]
[402060]
[402080]
[4020A0]
[4020C0]
[4020E0]
[404000]
[404020]
[404040]
[404060]
[404080]
[4040A0]
[4040C0]
[406000]
[406020]
[406040]
[406060]
[406080]
[4060A0]
[408000]
[408020]
[408040]
[408060]
[408080]
[40A000]
[40A020]
[40A040]
[40A060]
[40A080]
[40A0A0]
[40A0C0]
[40A0E0]
[40A0FE]
[40C000]
[40C020]
[40C040]
[40C060]
[40C080]
[40C0A0]
[40C0C0]
[40C0E0]
[40C0FE]
[40E000]
[40E020]
[40E040]
[40E060]
[40E080]
[40E0A0]
[40E0C0]
[40E0E0]
[40E0FE]
[40EF00]
[40EF20]
[40EF40]
[40EF60]
[40EF80]
[40EFA0]
[40EFC0]
[40EFE0]
[40EFFE]
[600000]
[600020]
[600040]
[600060]
[600080]
[6000A0]
[6000C0]
[6000E0]

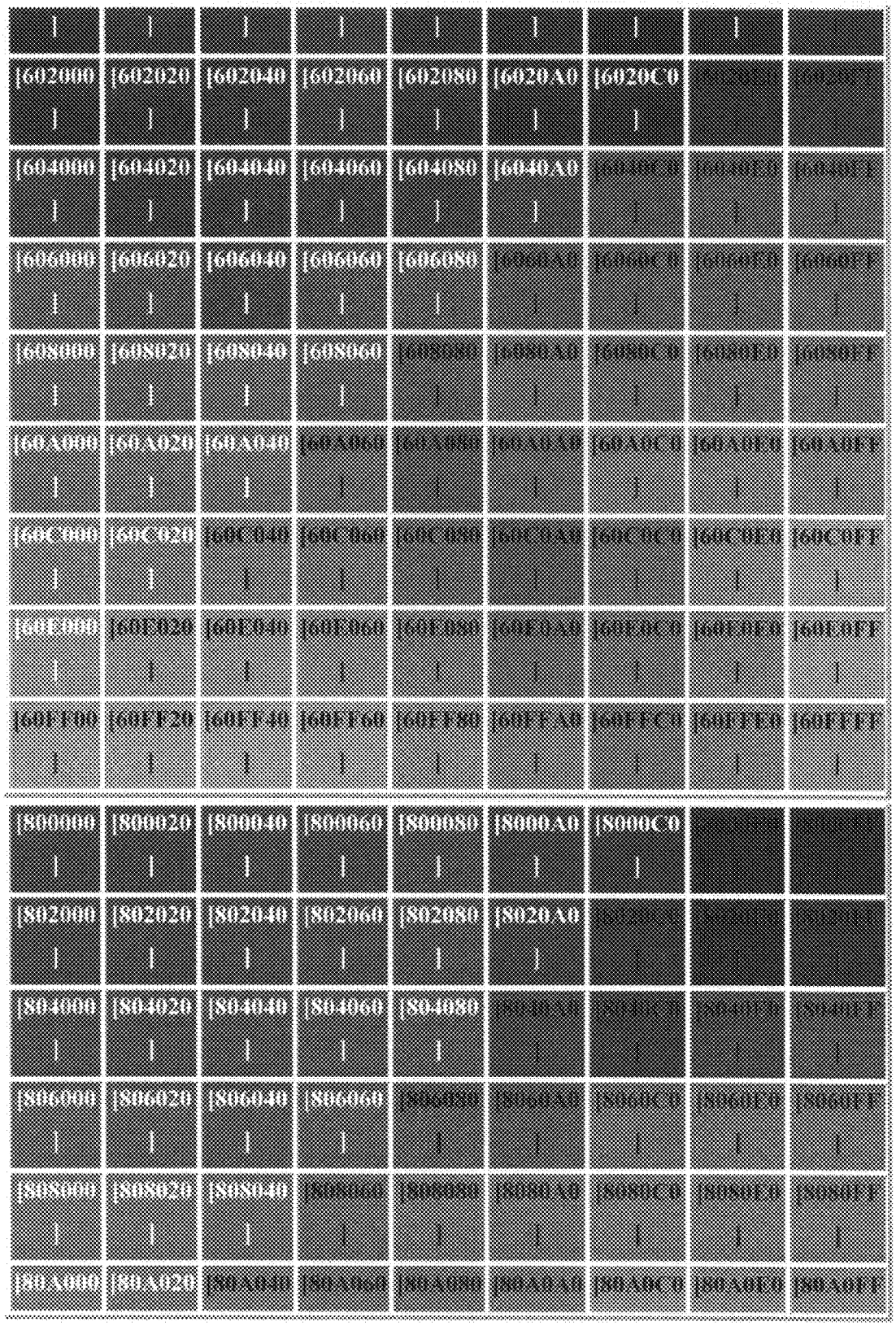
602000
602020
602040
602060
602080
6020A0
6020C0
604000
604020
604040
604060
604080
6040A0
6040C0
6040E0
6040FF
606000
606020
606040
606060
606080
6060A0
6060C0
6060E0
6060FF
608000
608020
608040
608060
608080
6080A0
6080C0
6080E0
6080FF
60A000
60A020
60A040
60A060
60A080
60A0A0
60A0C0
60A0E0
60A0FF
60C000
60C020
60C040
60C060
60C080
60C0A0
60C0C0
60C0E0
60C0FF
60E000
60E020
60E040
60E060
60E080
60E0A0
60E0C0
60E0E0
60E0FF
60FF00
60FF20
60FF40
60FF60
60FF80
60FFA0
60FFC0
60FFE0
60FFFF
800000
800020
800040
800060
800080
8000A0
8000C0
802000
802020
802040
802060
802080
8020A0
804000
804020
804040
804060
804080
8040A0
8040C0
8040E0
8040FF
806000
806020
806040
806060
806080
8060A0
8060C0
8060E0
8060FF
808000
808020
808040
808060
808080
8080A0
8080C0
8080E0
8080FF
80A000
80A020
80A040
80A060
80A080
80A0A0
80A0C0
80A0E0
80A0FF

| | | | | | | | | |
|---|---|---|---|---|---|---|---|---|
| \| | \| | \| | \| | \| | \| | \| | \| | \| |
| \|80C000\| | \|80C020\| | \|80C040\| | \|80C060\| | \|80C080\| | \|80C0A0\| | \|80C0C0\| | \|80C0E0\| | \|80C0FF\| |
| \|80E000\| | \|80E020\| | \|80E040\| | \|80E060\| | \|80E080\| | \|80E0A0\| | \|80E0C0\| | \|80E0E0\| | \|80E0FF\| |
| \|80FF00\| | \|80FF20\| | \|80FF40\| | \|80FF60\| | \|80FF80\| | \|80FFA0\| | \|80FFC0\| | \|80FFE0\| | \|80FFFF\| |
| \|A00000\| | \|A00020\| | \|A00040\| | \|A00060\| | \|A00080\| | \|A000A0\| | \|A000C0\| | \|A000E0\| | \|A00FFF\| |
| \|A02000\| | \|A02020\| | \|A02040\| | \|A02060\| | \|A02080\| | \|A020A0\| | \|A020C0\| | \|A02FE0\| | \|A02FFF\| |
| \|A04000\| | \|A04020\| | \|A04040\| | \|A04060\| | \|A04080\| | \|A040A0\| | \|A040C0\| | \|A04FE0\| | \|A04FFF\| |
| \|A06000\| | \|A06020\| | \|A06040\| | \|A06060\| | \|A06080\| | \|A060A0\| | \|A060C0\| | \|A06FE0\| | \|A06FFF\| |
| \|A08000\| | \|A08020\| | \|A08040\| | \|A08060\| | \|A08080\| | \|A080A0\| | \|A080C0\| | \|A08FE0\| | \|A08FFF\| |
| \|A0A000\| | \|A0A020\| | \|A0A040\| | \|A0A060\| | \|A0A080\| | \|A0A0A0\| | \|A0A0C0\| | \|A0A0E0\| | \|A0A0FF\| |
| \|A0C000\| | \|A0C020\| | \|A0C040\| | \|A0C060\| | \|A0C080\| | \|A0C0A0\| | \|A0C0C0\| | \|A0C0E0\| | \|A0C0FF\| |
| \|A0E000\| | \|A0E020\| | \|A0E040\| | \|A0E060\| | \|A0E080\| | \|A0E0A0\| | \|A0E0C0\| | \|A0E0E0\| | \|A0E0FF\| |
| \|A0FF00\| | \|A0FF20\| | \|A0FF40\| | \|A0FF60\| | \|A0FF80\| | \|A0FFA0\| | \|A0FFC0\| | \|A0FFE0\| | \|A0FFFF\| |
| \|C00000\| | \|C00020\| | \|C00040\| | \|C00060\| | \|C00080\| | \|C000A0\| | \|C000C0\| | \|C000E0\| | \|C00FFF\| |
| \|C02000\| | \|C02020\| | \|C02040\| | \|C02060\| | \|C02080\| | \|C020A0\| | \|C020C0\| | \|C02FE0\| | \|C02FFF\| |

| | | | | | | | | |
|---|---|---|---|---|---|---|---|---|
| ] | ] | ] | ] | ] | ] | ] | ] | ] |
| [C04000 ] | [C04020 ] | [C04040 ] | [C04060 ] | [C04080 ] | [C040A0 ] | [C040C0 ] | [C040E0 ] | [C040FF ] |
| [C06000 ] | [C06020 ] | [C06040 ] | [C06060 ] | [C06080 ] | [C060A0 ] | [C060C0 ] | [C060E0 ] | [C060FF ] |
| [C08000 ] | [C08020 ] | [C08040 ] | [C08060 ] | [C08080 ] | [C080A0 ] | [C080C0 ] | [C080E0 ] | [C080FF ] |
| [C0A00 0] | [C0A02 0] | [C0A04 0] | [C0A06 0] | [C0A08 0] | [C0A0A 0] | [C0A0C 0] | [C0A0E 0] | [C0A0F F] |
| [C0C00 0] | [C0C02 0] | [C0C04 0] | [C0C06 0] | [C0C08 0] | [C0C0A 0] | [C0C0C 0] | [C0C0E 0] | [C0C0F F] |
| [C0E00 0] | [C0E02 0] | [C0E04 0] | [C0E06 0] | [C0E08 0] | [C0E0A 0] | [C0E0C 0] | [C0E0E 0] | [C0E0F F] |
| [C0FF0 0] | [C0FF2 0] | [C0FF4 0] | [C0FF6 0] | [C0FF8 0] | [C0FFA 0] | [C0FFC 0] | [C0FFE 0] | [C0FFF F] |

| | | | | | | | | |
|---|---|---|---|---|---|---|---|---|
| [E00000 ] | [E00020 ] | [E00040 ] | [E00060 ] | [E00080 ] | [E000A0 ] | [E000C0 ] | [E000E0 ] | [E000FF ] |
| [E02000 ] | [E02020 ] | [E02040 ] | [E02060 ] | [E02080 ] | [E020A0 ] | [E020C0 ] | [E020E0 ] | [E020FF ] |
| [E04000 ] | [E04020 ] | [E04040 ] | [E04060 ] | [E04080 ] | [E040A0 ] | [E040C0 ] | [E040E0 ] | [E040FF ] |
| [E06000 ] | [E06020 ] | [E06040 ] | [E06060 ] | [E06080 ] | [E060A0 ] | [E060C0 ] | [E060E0 ] | [E060FF ] |
| [E08000 ] | [E08020 ] | [E08040 ] | [E08060 ] | [E08080 ] | [E080A0 ] | [E080C0 ] | [E080E0 ] | [E080FF ] |
| [E0A00 0] | [E0A02 0] | [E0A04 0] | [E0A06 0] | [E0A08 0] | [E0A0A 0] | [E0A0C 0] | [E0A0E 0] | [E0A0F F] |
| [E0C00 | [E0C02 | [E0C04 | [E0C06 | [E0C08 | [E0C0A | [E0C0C | [E0C0E | [E0C0F |

| | | | | | | | | |
|---|---|---|---|---|---|---|---|---|
| 0] | 0] | 0] | 0] | 0] | 0] | 0] | 0] | F] |
| [E0E00 0] | [E0E02 0] | [E0E04 0] | [E0E06 0] | [E0E08 0] | [E0E0A 0] | [E0E0C 0] | [E0E0E 0] | [E0E0F F] |
| [E0FF0 0] | [E0FF2 0] | [E0FF4 0] | [E0FF6 0] | [E0FF8 0] | [E0FFA 0] | [E0FFC 0] | [E0FFE 0] | [E0FFF F] |
| [FF0000 ] | [FF0020 ] | [FF0040 ] | [FF0060 ] | [FF0080 ] | [FF00A0 ] | [FF00C0 ] | [FF00E0 ] | [FF00FF ] |
| [FF2000 ] | [FF2020 ] | [FF2040 ] | [FF2060 ] | [FF2080 ] | [FF20A0 ] | [FF20C0 ] | [FF20E0 ] | [FF20FF ] |
| [FF4000 ] | [FF4020 ] | [FF4040 ] | [FF4060 ] | [FF4080 ] | [FF40A0 ] | [FF40C0 ] | [FF40E0 ] | [FF40FF ] |
| [FF6000 ] | [FF6020 ] | [FF6040 ] | [FF6060 ] | [FF6080 ] | [FF60A0 ] | [FF60C0 ] | [FF60E0 ] | [FF60FF ] |
| [FF8000 ] | [FF8020 ] | [FF8040 ] | [FF8060 ] | [FF8080 ] | [FF80A0 ] | [FF80C0 ] | [FF80E0 ] | [FF80FF ] |
| [FFA00 0] | [FFA02 0] | [FFA04 0] | [FFA06 0] | [FFA08 0] | [FFA0A 0] | [FFA0C 0] | [FFA0E 0] | [FFA0F F] |
| [FFC00 0] | [FFC02 0] | [FFC04 0] | [FFC06 0] | [FFC08 0] | [FFC0A 0] | [FFC0C 0] | [FFC0E 0] | [FFC0F F] |
| [FFE00 0] | [FFE02 0] | [FFE04 0] | [FFE06 0] | [FFE08 0] | [FFE0A 0] | [FFE0C 0] | [FFE0E 0] | [FFE0F F] |
| [FFFF0 0] | [FFFF2 0] | [FFFF4 0] | [FFFF6 0] | [FFFF8 0] | [FFFFA 0] | [FFFFC 0] | [FFFFE 0] | [FFFFF F] |